United States Patent [19]

Mitsche et al.

[11] 4,179,581

[45] Dec. 18, 1979

[54] PARAFFINIC HYDROCARBON ISOMERIZATION PROCESS

[75] Inventors: Roy T. Mitsche, Wauconda; George N. Pope, McHenry, both of Ill.

[73] Assignee: UOP Inc., Des Plaines, Ill.

[21] Appl. No.: 921,159

[22] Filed: Jun. 30, 1978

Related U.S. Application Data

[63] Continuation-in-part of Ser. No. 788,376, Apr. 18, 1977, Pat. No. 4,098,874.

[51] Int. Cl.$^2$ ............................ C07C 5/28; C07C 5/30
[52] U.S. Cl. .................................. 585/744; 585/746; 585/751
[58] Field of Search ...................... 260/683.65, 683.68, 260/683.7; 252/466 PT, 442

[56] References Cited

U.S. PATENT DOCUMENTS

| | | | |
|---|---|---|---|
| 3,642,925 | 2/1972 | Rausch | 260/683.65 |
| 3,969,425 | 7/1976 | Hayes | 260/683.65 |
| 4,098,874 | 7/1978 | Mitsche et al. | 252/466 PT |

*Primary Examiner*—George Crasanakis
*Attorney, Agent, or Firm*—James R. Hoatson, Jr.; John G. Cutts, Jr.; William H. Page, II

[57] ABSTRACT

Isomerizable hydrocarbons including paraffins, cycloparaffins, olefins and alkyl aromatics are isomerized by contacting the hydrocarbon at isomerization conditions with a catalytic composite comprising a platinum group metal on an alpha-alumina monohydrate support wherein said support is prepared by admixing an alpha-alumina monohydrate with an aqueous ammoniacal solution having a pH of at least about 7.5 to form a stable suspension and commingling said suspension with a salt of a strong acid to form an extrudable paste or dough. Upon extrusion, the extrudate is dried and calcined to form said alumina support.

17 Claims, No Drawings

PARAFFINIC HYDROCARBON ISOMERIZATION PROCESS

CROSS-REFERENCE TO RELATED APPLICATIONS

This application is a continuation-in-part of copending application Ser. No. 788,376 filed Apr. 18, 1977 and now U.S. Pat. No. 4,098,874 which issued on July 4, 1978. The teachings of which application are incorporated herein by reference thereto.

BACKGROUND OF THE INVENTION

This invention relates to a process for isomerizing isomerizable hydrocarbons, and in particular, isomerizable paraffins, cycloparaffins, olefins and alkylaromatic. More particularly, this invention relates to a process for isomerizing isomerizable hydrocarbons with a catalytic composite comprising a combination of a platinum group metal component, and an alpha-alumina monohydrate support wherein said support is prepared by admixing a finely divided alpha-alumina monohydrate with an aqueous ammoniacal solution having a pH of at least about 7.5 and forming a stable suspension, commingling a metal salt of a strong acid with said suspension and converting the suspension to an extrudable paste or dough, extruding the paste or dough, drying and calcining the extruded alumina.

Isomerization processes for the isomerization of hydrocarbons have acquired significant importance within the petrochemical and petroleum refining industry. The demand for the xylene isomers, particularly para-xylene, has resulted in the need for processes for isomerizing xylenes and ethylbenzene to obtain a desired xylene isomer such as para-xylene. Also, the need for branched chain paraffins such as isobutane or isopentane as intermediates for the production of high octance motor fuel produced by alkylation, it is desired that the final alkylate be highly branched. This can be accomplished by alkylating isobutane or isopentane with a $C_4$–$C_7$ internal olefin which, in turn, can be produced by the isomerization of the linear alphaolefin by shifting the double bond to a more central position.

SUMMARY OF THE INVENTION

Accordingly, it is an object of this invention to provide a process for isomerizing isomerizable hydrocarbons. More specifically, it is an object of this invention to provide an isomerization process using a particular isomerization catalyst effective in isomerizing isomerizable hydrocarbons without introducing undesired decomposition reactions.

In a broad embodiment, this invention relates to a process for isomerizing an isomerizable hydrocarbon which comprises contacting said hydrocarbon with a catalytic composite comprising a combination of a platinum group metal component, and an alumina support wherein said support is prepared by admixing a finely divided alpha-alumina monohydrate with an aqueous ammoniacal solution having a pH of at least about 7.5 and forming a stable suspension, commingling a metal salt of a strong acid with said suspension and converting the suspension to an extrudable paste or dough, extruding the paste or dough, drying and calcining the extruded alumina.

In a more specific embodiment, this invention relates to the isomerization of either a saturated or olefinic isomerizable hydrocarbon by contacting the hydrocarbon with the aforementioned catalytic composite at isomerization conditions which include a temperature of about 0° C. to about 425° C., a pressure of about atmospheric to about 100 atmospheres, and a liquid hourly space velocity of about 0.1 to about 20.0 hr.$^{-1}$.

In another limited embodiment, this process relates to the isomerization of an isomerizable alkylaromatic hydrocarbon by contacting an alkylaromatic with the aforementioned catalytic composite at isomerization conditions which include a temperature of about 0° C. to about 600° C., a pressure of about atmospheric to about 100 atmospheres, a liquid hourly space velocity of about 0.1 to about 20.0 hr.$^{-1}$ and a hydrogen to hydrocarbon mole ratio of about 0.5:1 to about 20:1.

In a more specific embodiment, the catalytic composite used in isomerizing the foregoing isomerizable hydrocarbons contains, on an elemental basis 0.1 to about 5 weight percent halogen and about 0.1 to about 2 weight percent platinum group metal.

In another embodiment, this invention relates to a catalytic composite which comprises alumina, having combined therewith platinum group metallic component and a Friedel-Crafts metal halide component.

Other objects and embodiments referring to alternative isomerizable hydrocarbons and to alternative catalytic compositions will be found in the following further detailed description of this invention.

DETAILED DESCRIPTION

The process of this invention is applicable to the isomerization of isomerizable saturated hydrocarbons including acyclic paraffins and cyclic naphthenes and is particularly suitable for the isomerization of straight chain or mildly branched chain paraffins containing 4 or more carbon atoms per molecule such as normal butane, normal pentane, normal hexane, normal heptane, normal octane, etc., and mixtures thereof. Cycloparaffins applicable are those ordinarily containing at least 5 carbon atoms in the ring such as alkylcyclopentanes and cyclohexanes, including methylcyclopentane, dimethylcyclopentane, cyclohexane, methylcyclohexane, dimethylcyclohexane, etc. This process also applies to the conversion of mixtures of paraffins and/or naphthenes such as those derived by selective fractionation and distillation of straight-run natural gasolines and naphthas. Such mixtures of paraffins and/or naphthenes include the so-called pentane fractions, hexane fractions, and mixtures thereof. It is not intended to limit this invention to these enumerated saturated hydrocarbons, and it is contemplated that straight or branched chain saturated hydrocarbon containing up to about 20 carbon atoms per molecule may be isomerized according to the process of the present invention with $C_4$–$C_7$ n-alkanes being particularly preferred.

The olefins applicable within this isomerization process are generally a mixture of olefinic hydrocarbons of approximately the same molecular weight, including the 1-isomer, 2-isomer, and other position isomers, capable of undergoing isomerization to an olefin in which the double bond occupies a more centrally located position in the hydrocarbon chain. The process of this invention can be used to provide an olefinic feed stock for motor fuel alkylation purposes containing an optimum amount of the more centrally located double bond isomers, by converting the 1-isomer, or other near terminal position isomer into olefins wherein the double bond is more centrally located in the carbon atoms chain. The process of this invention is also applicable to the isomerization of such isomerizable olefinic hydrocarbons such as the isomerization of 1-butene to 2-butene or the isomerization of the 3-methyl-1-butene to 2-methyl-2-butene. Also, the process of this invention can be utilized to shift the double bond of an olefinic hydrocarbon such as 1-pentene, 1-hexene, 2-hexene, and 4-methyl-1-pentene to a more centrally located position so that 2-pentene, 2-hexene, 3-hexene and 4-methyl-2-pentene, respectively, can be obtained. It is not intended to limit this invention to these enumerated olefinic hydrocarbons as it is contemplated that shifting of the double bond to a more centrally located position may be effective in straight or branched chain olefinic hydrocarbons containing up to about 20 carbon atoms per molecule. Preferred are linear $C_4$–$C_7$ alpha-mono-olefins. The process of this invention also applies to the hydroisomerization of olefins wherein olefins are converted to branched-chain paraffins.

Further, the process of this invention is also applicable to the isomerization of isomerizable alkylaromatic hydrocarbons including ortho-xylene, meta-xylene, para-xylene, ethylbenzene, the ethyltoluenes, the trimethylbenzenes, the diethylbenzenes, the triethylbenzenes, normal propylbenzene, isopropylbenzene, etc., and mixtures thereof. Preferred isomerizable alkylaromatic hydrocarbons are the monocyclic alkylaromatic hydrocarbons, that is, the alkyl benzene hydrocarbons, particularly the $C_8$ alkylbenzenes, and nonequilibrium mixtures of the various $C_8$ aromatic isomers.

These foregoing isomerizable hydrocarbons may be derived as selective fractions from various naturally-occurring petroleum streams either as individual components or as certain boiling range fractions obtained by the selective fractionation and distillation of catalytically cracked gas oil. Thus, the process of this invention may be successfully applied to and utilized for complete conversion of isomerizable hydrocarbons when these isomerizable hydrocarbons are present in minor quantities in various fluid or gaseous streams. Thus, the isomerizable hydrocarbons for use in the process of this invention need not be concentrated. For example, isomerizable hydrocarbons appear in minor quantities in various refinery streams, usually diluted with gases such as hydrogen, nitrogen, methane, ethane, propane, etc. These refinery streams containing minor quantities of isomerizable hydrocarbons are obtained in petroleum refineries and various refinery installation including thermal cracking units, catalytic cracking units, thermal reforming units, coking units, polymerization units, dehydrogenation units, etc. Such refinery offstreams have in the past often been burned for fuel value, since an economical process for the utilization of the hydrocarbon content has not been available. This is particularly true for refinery fluid streams known as off gas streams containing minor quantities of isomerizable hydrocarbons.

As indicated in the embodiments, the catalyst utilized in the present isomerization process comprises a platinum group metal component, and a halogen component incorporated on alpha-alumina monohydrate support material.

The alpha-alumina monohydrate employed herein is preferably an alpha-alumina monohydrate derived from the water hydrolysis of an aluminum alkoxide. More preferably, the alpha-alumina monohydrate is a product of the well-known Ziegler process. The alpha-alumina monohydrate is thus preferably prepared stepwise starting with the reaction of aluminum, hydrogen and ethylene. After a further polymerization step with ethylene, the trialkyl aluminum polymerization product is oxidized to form an aluminum alkoxide which, on subsequent water hydrolysis, yields an alumina slurry and an alcohol product. The alumina recovered from the reaction mixture is generally treated for the removal of residual alcohols, for example by solvent extraction, and/or steam stripping, and then dried to produce the alpha-alumina monohydrate in a finely divided state.

Pursuant to the present invention, the finely divided alpha-alumina monohydrate is admixed with an aqueous alkaline solution having a pH of at least about 7.5, and preferably from about 7.5 to about 8.5. The alpha-alumina monohydrate added to the stirred aqueous alkaline solution forms a stable suspension having the consistency of a light whipped cream—the suspension being Newtonian in character with little if any thixotropic or dilatant behavior.

The alumina is preferably admixed with a sufficient amount of aqueous solution to provide an extrudable paste or dough comprising from about 30 to about 60 wt. % alumina. The aqueous alkaline solution is preferably an aqueous ammoniacal solution. Suitable ammoniacal solutions include solutions of bases such as ammonium hydroxide, hydroxylamine, hydrazine, tetramethylammonium hydroxide, etc., or a strong organic amine like methylamine, dimethylamine, ethylamine, diethylamine, propylamine, diisopropylamine, n-butylamine, t-butylamine, diisobutylamine, n-amylamine, n-hexylamine, ethylenediamine, hexamethylenediamine, benzylamine, aniline, piperizine, piperadine, and the like, the selected base being employed in sufficient concentration to provide a pH of at least about 7.5, and preferably from about 7.5 to about 8.5.

With the addition of a metal salt of a strong acid to the stirred suspension as herein contemplated, the suspension becomes very fluid for a brief period permitting the suspension to become thoroughly and uniformly mixed before setting to a firm extrudable paste. The selected metal salt is conveniently an aluminum salt whereby the aluminum provides a portion of the alumina of the finished product. However, the metal salt may comprise one or more metals exhibiting a catalytic effect with respect to one or more hydrocarbon conversion reactions whereby said metal or metals appear as a catalytic component of the final alumina product. The metal salt is suitably added to the stirred suspension as an aqueous solution thereof in an amount to provide sufficient acid anions to convert said suspension to an extrudable paste, an amount which is usually equivalent to that required to provide from about 1 to about 10 wt. % of the metal content of the finished product. Suitable metal salts of a strong acid particularly include the nitrates, sulfates and halides, and especially the nitrates, for example, aluminum nitrate, ferric nitrate, nickel nitrate, cobalt nitrate, chromium nitrate, copper nitrate, palladium nitrate, silver nitrate, zinc nitrate, stannous and stannic nitrate and the like.

Extrusion of the paste or dough can be effected in accordance with prior art practice. Thus, utilizing a conventional screw type extruder, the dough or paste is processed through a die plate generally comprising orifice openings in the 1/32–¼ inch diameter range. The freshly extruded material may be collected in the form of strands of indefinite or random lengths to be dried and subsequently broken into extrudate particles; or the freshly extruded material may be cut into random or predetermined lengths and subsequently dried; or the freshly extruded material may be formed into spheres, for example, by the process whereby the extrudate strands are collected in a spinning drum—the strands becoming segmented and spheroidized under the spinning influence of the drum.

In any case, the extrudate is dried and subsequently calcined. Suitable drying is accomplished at a temperature of from about 100° to about 120° C. in an air atmosphere using a forced draft oven. The extrudate product can be dried and calcined at a temperature of from about 450° to about 850°, but preferably at a temperature of from about 550° to about 750° C. in a flow of air containing 1 to 5 wt. % steam to produce a calcined product having a surface area of from about 165 to about 215 m$^2$/g and a pore volume of from about 0.3 to about 0.4 cc/g and the pore diameter range of from about 20 to about 80 Angstroms.

An essential constituent of the catalyst of the present invention is a halogen component. Although the precise form of the chemistry of the association of the halogen component with the alumina support is not entirely known, it is customary in the art to refer to the halogen component as being combined with the alumina support, or with the other ingredients of the catalyst. This combined halogen may be either fluorine, chlorine, iodine, bromine, or mixtures thereof. Of these, fluorine and particularly, chlorine are preferred for the purposes of the present invention. In addition, fluorine and chlorine may be utilized together. The halogen may be added to the alumina support in any suitable manner, either during preparation of the support or before or after the addition of the catalytically active metallic components. For example, the halogen may be added, at any stage of the preparation of the support or to the calcined support, as an aqueous solution of an acid such as hydrogen fluoride, hydrogen chloride, hydrogen bromide, etc., or as an acid salt such as ammonium bifluoride, etc. The halogen component or a portion thereof, may be composited with alumina during the impregnation of the latter with the platinum group component; for example, through the utilization of a mixture of chloroplatinic acid and hydrogen chloride. In any event, the halogen will be typically composited with the alumina support in such a manner as to result in a final composite that contains on an elemental basis, about 0.1 percent to about 5 percent and preferably about 0.4 to about 1 percent by weight of chlorine when chlorine is used as the halogen or about 0.5 to about 3.5 percent by weight when fluorine is utilized.

As indicated above, the catalyst of the present invention also contains a platinum group metallic component. Although the process of the present invention is specifically directed to the use of a catalytic composite containing platinum, it is intended to include other platinum group metals such as palladium, rhodium, ruthenium, etc. Preferred is platinum, palladium and compounds thereof. The platinum group metallic component, such as platinum, may exist within the final catalytic composite as a compound such as an oxide, sulfide, halide, etc., or as an elemental state. Generally, the amount of the platinum group metallic component present in the final catalyst is small compared to the quantities of the other components combined therewith. In fact, the platinum group metallic component generally comprises about 0.01 to about 1 percent weight of the final catalytic composite calculated on an elemental basis. Excellent results are obtained when the catalyst contains about 0.3 to about 0.9 wt. percent of the platinum group metal.

The platinum group metal component is suitably composited with the support or carrier material by impregnation and/or ion-exchange techniques familiar to the art. For example, a soluble platinum group compound, that is, a soluble compound of platinum, palladium, rhodium, ruthenium, osmium and/or iridium, is prepared in aqueous solution, and the alumina particles soaked, dipped, or otherwise immersed therein. Suitable platinum group compounds include platinum chloride, chloroplatinic acid, ammonium chloroplatinate, dinitrodiaminoplatinum, palladium chloride, and the like. It is common practice to impregnate the support or carrier material with an aqueous chloroplatinic acid solution acidified with hydrochloric acid to facilitate an even distribution of platinum on the support or carrier material. The support or carrier material is preferably maintained in contact with the impregnating solution at ambient temperature conditions, suitably for at least about 30 minutes, and the impregnating solution thereafter evaporated to dryness. For example, a volume of the particulate support or carrier material is immersed in a substantially equal volume of impregnating solution in a steam jacketed rotary dryer and tumbled therein for a brief period at about room temperature. Steam is thereafter applied to the dryer jacket to expedite evaporation of the impregnating solution and recovery of substantially dry impregnated particles. Thus, a further embodiment of this invention relates to an alumina support or carrier material characterized by a surface area of from about 165 to about 215 m$^2$/g and a pore volume of from about 0.3 to about 0.4 cc/g in the pore diameter range of from about 20 to about 80 Angstroms, said alumina being impregnated with from about 0.1 to about 2 wt. % platinum.

The alumina composition of this invention is useful as a support or carrier material for a platinum group metal component alone or in combination with a tin component, a rhenium component, and/or a germanium component. The tin, rhenium, and/or germanium components may be composited with the support or carrier material in any conventional or otherwise convenient manner. Suitable methods include impregnation and/or ion-exchange of the support or carrier material with a suitable compound of one or more of said components in any desired sequence, with or without intermediate calcination. In the impregnation of the support or carrier material, it is a preferred practice to impregnate one or more of said components on said support or carrier material simultaneously with the platinum group metal component from a common impregnating solution. For example, when the added component is tin, stannic chloride is conveniently and advantageously prepared in common solution with chloroplatinic acid, the concentration of each component therein being sufficient to yield a catalyst product containing from about 0.01 to about 2 weight percent platinum and from about 0.1 to about 5 weight percent tin calculated as the elemental metal. Similarly, when the desired added component is rhenium, perrhenic acid and chloroplatinic acid can be prepared in a common aqueous solution to impregnate the support or carrier material, suitably with from about 0.01 to about 2 weight percent platinum and from about 0.01 to about 2 weight percent rhenium. Thus, another embodiment of this invention concerns an alumina support or carrier material characterized by a surface area of from about 165 to about 215 m$^2$/g and a pore volume of from about 0.3 to about 0.4 cc/g in the pore diameter range from about 20 to about 80 Angstroms, said alumina being impregnated with from about 0.01 to about 2 wt. % platinum and from about 0.01 to about 2 wt. % rhenium.

The tin, rhenium, and/or germanium components and particularly the tin, and germanium components are advantageously composited with the alumina by including a suitable acid salt thereof in the aforementioned suspension prepared by admixing a finely divided alpha-alumina monohydrate with an aqueous alkaline solution. For example, an acid salt of tin such as stannous or stannic chloride, may be admixed with said suspension and serve not only as a precursor of the desired tin component, but also as the metal salt of a strong acid as herein contemplated. Following the extrusion process and subsequent calcination, the alumina is obtained comprising the tin component in intimate combination therewith and suitable for further impregnation and/or ion exchange to incorporate, for example, the platinum group metal component.

Although not essential, the resulting catalytic composite can be impregnated with an anhydrous Friedel-Crafts type metal halide, particularly aluminum chloride. Other suitable metal halides are aluminum bromide, ferric chloride, ferric bromide, zinc chloride, beryllium chloride, etc. This impregnation can be accomplished by the sublimination of the aluminum chloride onto the platinum alumina composite under conditions such that the sublimed aluminum chloride is chemically combined with the hydroxyl groups of the composite. This reaction is accompanied by the elimination of from about 0.5 to about 2.0 moles of hydrogen chloride per mole of aluminum chloride reacted. Since aluminum chloride sublimes at about 184° C. suitable impregnation temperatures range from about 190° C. to about 700° C.; preferably, 200° C. to about 600° C. The sublimation can be conducted at atmospheric pressure or under increased pressures and in the presence of diluents such as inert gases, hydrogen and light paraffinic hydrocarbons. The impregnation may be conducted batchwise but a preferred method is to pass sublimed $AlCl_3$ vapors in admixture with an inert gas such as $H_2$ through the calcined catalyst bed. This method both continuously deposits the $AlCl_3$ and removes the evolved HCl.

The amount of metal halide combined with the catalytic composite may range from about 5 to about 100 weight percent of the original composite. The final composite has unreacted metal halide removed by treating the composite at a temperature above 300° C. for a time sufficient to remove therefrom any unreacted metal halide. For aluminum chloride, temperatures of about 400° C. to about 600° C. and times of from about 1 to about 48 hours are satisfactory. The reaction of the aluminum chloride with the hydroxyl groups of the alumina composite yields — Al—O—$AlCl_2$ active centers which can enhance the performance characteristics of the original catalytic composite, particularly for $C_4$-$C_7$ n-alkanes.

In addition, the resulting reduced catalytic composite may in some cases be beneficially subjected to a presulfiding operation designed to incorporate in the catalytic composite from about 0.05 to about 5 weight percent sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 50° F. up to about 1100° F. or more.

According to the present invention, the isomerizable hydrocarbon, in admixture with hydrogen, is contacted with a catalyst of the type described above in a hydrocarbon conversion zone. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use a fixed bed system. In this system a hydrogen-rich gas and the charge stock are preheated by any suitable heating means to the desired reaction temperature and then are passed into a conversion zone containing a fixed bed of the catalyst type previously characterized. It is, of course, understood that the conversion zone may be one or more separate reactors with suitable means therebetween to insure that the desired conversion temperature is maintained at the entrance to each reactor. It is also to be noted that the reactants may be contacted with the catalyst bed in either upward, downward, or radial flow fashion. In addition, it is to be noted that the reactants may be in the liquid phase, a mixed liquid-vapor phase, or a vapor phase when they contact the catalyst, with best results obtained in the vapor phase.

The process of this invention, utilizing the catalyst hereinbefore set forth, for isomerizing isomerizable olefinic or saturated hydrocarbons is preferably effected in a continuous flow, fixed bed system. One particular method is continuously passing the hydrocarbon to a reaction zone containing the catalyst and maintaining the zone at proper isomerization conditions such as a temperature in the range of about 0° to about 425° C. or more, and a pressure of about atmospheric to about 200 atmospheres or more. The hydrocarbon is passed over the catalyst at a liquid hourly space velocity (defined as volume of liquid hydrocarbon passed per hour per volume of catalyst) of from about 0.1 to about 20 hr.$^{-1}$ or more. In addition, diluents such as argon, nitrogen, or hydrogen may be present. In fact, the presence of hydrogen at a hydrogen to hydrocarbon mole ratio of about 0.1:1 to about 10:1 is preferred. The isomerized product is continuously withdrawn, separated from the reactor effluent, and recovered by conventional means, preferably fractional distillation, while the unreacted starting material may be recycled to form a portion of the feed stock.

Likewise, the process of this invention for isomerizing an isomerizable alkylaromatic hydrocarbon is also preferably effected by passing the aromatic to a reaction zone containing the hereinbefore described catalyst and maintaining the zone at proper alkylaromatic isomerization conditions such as a temperature in the range of about 0° C. to about 600° C. or more, and a pressure of atmospheric to about 100 atmospheres or more. The hydrocarbon is passed, in admixture with hydrogen, at a liquid hourly hydrocarbon space velocity of about 0.1 to about 20 hr.$^{-1}$ or more and a hydrogen to hydrocarbon mole ratio of about 0.5:1 to about 20:1. Other inert diluents such as nitrogen, argon, etc. may also be present. The isomerized product is continually withdrawn, separated from the reactor effluent by conventional means such as fractional distillation or crystallization, and recovered.

EXAMPLES

The following examples are given to illustrate the preparation of the catalyst composite to be utilized in the process of this invention and its use in the isomerization of isomerizable hydrocarbons. However, these examples are not presented for purposes of limiting the scope of the invention but in order to further illustrate the embodiment of the present process.

EXAMPLE I

In this example, representative of one preferred embodiment of this invention, 4000 grams of a finely divided alpha-alumina monohydrate (Catapal SB alumina) was added to a rapidly stirred aqueous alkaline solution having a pH of about 7.5. The alumina contained about 25 wt. % volatile matter, and the alkaline solution consisted of 12.9 cc of concentrated ammonium hydroxide diluted to 3450 cc of water. The resulting slurry was a stable suspension having a light creamy consistency. The suspension was Newtonian in character and gave no indication of thixotropic or dilatant behavior. After about 30 minutes of continuous stirring, an aluminum nitrate solution was added, the solution consisting of 595 grams of $Al(NO_3)_3$ $9H_2O$ dissolved in 1400 cc of water. The stirred suspension became very thin and extremely fluid for about 10 seconds and thereafter set to a thick paste with a solids content of about 33 wt. %. The paste was subsequently extruded, oven dried for about 12 hours at 110° C., and calcined for about 2 hours at 650° C. in air containing about 3 wt. % steam. The dried and calcined alumina product had a surface area of 217 m$^2$/g, and a pore volume of about 0.35 cc/g in the 40–60 Angstrom diameter range.

About 250 cc of the alumina particles were immersed in 250 cc of an impregnating solution. The impregnating solution was prepared by admixing 46.9 cc of chloroplatinic acid (10 milligrams of platinum per cc), and 21.3 cc of concentrated hydrochloric acid, the solution being diluted to 250 cc with water. The alumina particles were tumbled in the solution for about ½ hour at room temperature utilizing a steam jacketed rotary dryer. Steam was thereafter applied to the dryer jacket and the solution evaporated to dryness in contact with the tumbling particles. The particles were subsequently calcined in air for ½ hour at 390° F., and for an additional ½ hour at 975° C. The calcined particles were thereafter reduced in hydrogen for about 1 hour at 1050° F. to yield a catalyst comprising 0.22 wt. % platinum, and about 1.0 wt. % chloride. The average bulk density was approximately 0.84 grams per cc.

EXAMPLE II

A portion of the catalyst produced by the method of Example I is placed in a continuous flow, fixed-bed isomerization plant of conventional design. Substantially pure meta-xylene is used as the charge stock. The charge stock is commingled with about 8 moles of H$_2$ per mole of hydrocarbon, heated to about 400° C., and continuously charged to the reactor containing the catalyst which is maintained at about a pressure of about 300 psig. Substantial conversion of meta-xylene to para-xylene is obtained . . . i.e. greater than 80 percent of equilibrium.

EXAMPLE III

Another portion of the catalyst produced by Example I is used to isomerize ethylbenzene. The reactor is maintained at 300 psig. and 410° C. as ethylbenzene, commingled with 8 moles of H$_2$ per mole of ethylbenzene is continuously passed to the reactor at 2 LHSV. Substantial conversion of ethylbenzene to the three xylene isomers is observed.

EXAMPLE IV

Another portion of the catalyst produced by Example I is used to isomerize ortho-xylene to para-xylene. The reactor is maintained at a temperature of 400° C., and a pressure of 300 psig. as ortho-xylene, commingled with 8 moles of H$_2$ per mole of ortho-xylene is passed to the reactor at a liquid hourly space velocity (LHSV) of 2.0 hr.$^{-1}$. Substantial conversion—i.e. greater than 80 percent of equilibrium conversion—of ortho-xylene to para-xylene is obtained.

EXAMPLE V

A catalyst identical to that produced in Example I but containing only 0.40 wt. % combined chloride is used to isomerize 1-butene at a pressure of about 500 psig. and a temperature of about 140° C. in an appropriate continuous isomerization reactor. Substantial conversion to 2-butene is obtained.

EXAMPLE VI

Another portion of the catalyst utilized in Example V is charged to an appropriate continuous isomerization reactor maintained at a pressure of about 1000 psig. and a temperature of about 180° C. 3-methyl-1-butene is continuously passed to this reactor and a substantial conversion to 2-methyl-2-butene is obtained.

EXAMPLE VII

Another catalyst identical to that produced in Example I, except that the catalyst particles are contacted with hydrogen fluoride to provide a 2.7 weight percent combined fluoride content, is placed in an appropriate continuous isomerization reactor maintained at a pressure of about 300 psig. and a temperature of about 200° C. Normal hexane is continuously charged to the reactor and an analysis of the product stream shows substantial conversion to 2,2-dimethylbutane, 2,3-dimethylbutane, 2-methylpentane, and 3-methylpentane.

EXAMPLE VIII

One hundred grams of the reduced catalyst composite of Example I are placed in a glass-lined rotating autoclave along with 75 grams of anhydrous aluminum chloride. The autoclave is sealed, pressured with 25 psi of hydrogen and heated and rotated for 2 hours at 250° C. The autoclave is allowed to cool, depressured through a caustic scrubber, opened and the final composite removed therefrom. Weighing of this composite indicates a 15 wt. percent gain equivalent to the aluminum chloride sublimed and reacted thereon. The caustic scrubber is found to have absorbed hydrogen chloride equivalent to about 5.0 wt. percent of the original composite corresponding to about 0.8 mole of HCl per mole of ACl$_3$ adsorbed.

EXAMPLE IX

A portion of the catalyst of Example VIII is used to isomerize normal butane at a pressure of 300 psig., a 0.5 hydrogen to hydrocarbon mole ratio, and a 1.0 LHSV at a temperature of 230° C. Substantial conversion of n-butane to isobutane is observed—approximately a conversion of n-butane to isobutane of about 45 wt. % of the butane charge.

EXAMPLE X

Another portion of the catalyst of Example VII is placed in an appropriate continuous isomerization reactor maintained at a temperature of about 210° C. and a pressure of about 250 psig. Methylcyclopentane is continuously passed to this reactor and a substantial conversion to cyclohexane is observed.

EXAMPLE XI

In this example, 4000 grams of a finely divided alpha-alumina monohydrate (Catapal SB Alumina) was added to a rapidly stirred aqueous alkaline solution having a pH of about 7.5. The alumina contained about 25 wt. % volatile matter, and the alkaline solution of 12.9 cc of concentrated ammonium hydroxide diluted to 3450 cc with water. The resulting slurry was a stable suspension having a light creamy consistency. The suspension was Newtonian in character and gave no indication of thixotropic or dilatant behavior. After about 30 minutes of continuous stirring, an aluminum nitrate solution was added, the solution consisting of 595 grams of Al(NO$_3$)$_3$ 9 H$_2$O dissolved in 1400 cc of water. The stirred suspension became very thin and extremely fluid for about 10 seconds and thereafter set to thick paste with a solids content of about 33 wt. %. The paste was subsequently extruded, oven dried for about 12 hours at 110° C. and calcined for about 2 hours at 650° C. in air containing about 3 wt. % steam. The dried and calcined alumina product had a surface area of 217 m$^2$/g, and a pore volume of about 0.35 cc/g in the 40-60 Angstrom diameter range.

About 250 cc of the alumina particles are immersed in 250 cc of an impregnating solution containing chloroplatinic acid, hydrogen chloride and perrhenic acid in amounts sufficient to yield a final composite containing 0.60 wt. percent platinum, 0.2 wt. percent rhenium, and 0.85 wt. percent combined chloride—all calculated on an elemental basis. The alumina particles are tumbled in the solution for about ½ hour at room temperature utilizing a steam jacketed rotary dryer. Steam is thereafter applied to the dryer jacket and the solution is evaporated to dryness in contact with the tumbling particles. The particles are subsequently calcined in air for ½ hour at 390° F., and for an additional ½ hour at 975° F. The calcined particles are thereafter reduced in hydrogen for about 1 hour at 1050° F. to yield a finished catalyst.

EXAMPLE XII

A portion of the catalyst produced by the method of Example XI is placed in a continuous flow, fixed bed isomerization plant of conventional design. Substantially pure metaxylene is used as the charge stock. The charge stock is commingled with about 8 moles of H$_2$ per mole of hydrocarbon, heated to about 400° C. and continuously charged to the reactor containing the catalyst which is maintained at about a pressure of about 300 psig. Substantial conversion of meta-xylene to para-xylene is obtained . . . i.e., greater than 80 percent of equilibrium.

EXAMPLE XIII

One hundred grams of the reduced catalytic composite of Example XI are placed in a glass-lined rotating autoclave along with 75 grams of anhydrous aluminum chloride. The autoclave is sealed, pressured to 25 psig. with hydrogen and heated and rotated for 2 hours at 250° C. The autoclave is allowed to cool, depressured through a caustic scrubber, opened and the final composite removed therefrom. Weighing of this composite indicates a 15 weight percent gain equivalent to the aluminum chloride sublimed and reacted thereon.

EXAMPLE XIV

A portion of the catalyst of Example XIII is used to isomerize normal butane at a pressure of 300 psig., a 0.5 hydrogen to hydrocarbon mole ratio, and a 1 LHSV at a temperature of 230° C. Substantial conversion of n-butane to isobutane is observed—approximately a conversion of n-butane to isobutane of about 45 weight percent of the butane charge.

EXAMPLE XV

About 250 cc of dried and calcined alumina particles from Example XI are immersed in 250 cc of an impregnating solution containing chloroplatinic acid, hydrogen chloride and stannic chloride in amounts sufficient to yield a final composite containing 0.75 weight percent platinum and 0.5 weight percent tin, calculated on an elemental basis. The impregnated particles are then dried at a temperature of about 300° F. for about an hour and thereafter calcined in an air atmosphere at a temperature of about 925° F. for about 1 hour. The resulting calcined spheres are then contacted with an air stream containing H$_2$O and HCl in a mole ratio of about 40:1 for about 4 hours at 975° F.

EXAMPLE XVI

A portion of the catalyst prepared in Example XV is placed, as a catalytic composite, in a continuous flow fixed bed isomerization plant of conventional design. The charge stock, containing on a weight percent basis, 20% ethylbenzene, 10% para-xylene, 50% meta-xylene and 20% ortho-xylene is commingled with about 8 moles of hydrogen per mole of hydrocarbon, heated to 400° C., and continuously charged at 4 hr.$^{-1}$ liquid hourly space velocity (LHSV) to the reactor which is maintained at a pressure of about 400 psig. and 400° C. The resulting product evidences essentially equilibrium conversion to para-xylene with only insignificant amounts of cracked products thus indicating an efficient alkylaromatic isomerization catalyst.

EXAMPLE XVII

A portion of catalytic composite prepared in Example XV is placed in a glass-lined rotating autoclave along with anhydrous aluminum chloride. The autoclave is sealed, pressured to 25 psig. with hydrogen and heated and rotated for 2 hours at 300° C. The autoclave is then allowed to cool, depressured through a caustic scrubber, opened and the final composite removed therefrom. An analysis of this composite indicates a 15 weight percent gain based on the original composite, equivalent to the aluminum chloride sublimed and reacted thereon.

EXAMPLE XVIII

A portion of the catalyst prepared in Example XVII is placed in an appropriate continuous isomerization apparatus and used to isomerize normal butane at a reactor pressure of 300 psig., a 0.5 hydrogen to hydrocarbon mole ratio, a 1 LHSV, and a reactor temperature of 230° C. Substantial conversion of normal butane to isobutane is observed.

We claim as our invention:

1. A process for isomerizing an isomerizable paraffinic hydrocarbon which comprises contacting said paraffinic hydrocarbon, at isomerization conditions, with a catalytic composite comprising a combination of a platinum group metal component and an alumina support wherein said support is prepared by admixing a finely divided alpha-alumina monohydrate with an aqueous ammoniacal solution having a pH of at least about 7.5 to form a stable suspension, commingling a catalytic metal salt of a strong acid with said suspension to form the suspension into an extrudable paste or dough, extruding the paste or dough to form an extrudate, drying and calcining said extrudate to form said alumina support.

2. The process of claim 1 wherein said catalyst further comprises from about 0.01 to about 2 weight percent rhenium composited with said alumina.

3. The process of claim 1 wherein said catalyst further comprises from about 0.01 to about 2 weight percent germanium composited with said alumina.

4. The process of claim 1 wherein said catalyst further comprises from about 0.01 to about 5 weight percent tin composited with said alumina.

5. The process of claim 1 wherein said platinum group metal is platinum.

6. The process of claim 1 wherein said alumina is a water hydrolysis product of an aluminum alkoxide.

7. The process of claim 1 wherein said alumina is a water hydrolysis product of an aluminum alkoxide produced by the Ziegler process.

8. The process of claim 1 wherein said aqueous ammoniacal solution has a pH from about 7.5 to about 8.5.

9. The process of claim 1 wherein said metal salt is an aluminum salt of a strong acid.

10. The process of claim 1 wherein said metal salt is aluminum nitrate.

11. The process of claim 1 wherein said metal salt is an aluminum salt of a strong acid employed in an amount to provide from about 2 to about 10 weight percent of the alumina in the final product.

12. The process of claim 1 wherein said suspension comprises from about 30 to about 60 weight percent alumina.

13. The process of claim 1 wherein said alumina is calcined at a temperature of from about 550° to about 750° C. to provide a surface area from about 165 to about 215 m$^2$/g, and a pore volume from about 0.3 to about 0.4 cc/g in a pore diameter range of from about 20 to about 80 Angstroms.

14. The process of claim 1 wherein said isomerization conditions include a temperature of about 0° C. to about 425° C., a pressure of about atmospheric to about 100 atmospheres and a liquid hourly space velocity of about 0.1 to about 20.

15. The process of claim 14 wherein said paraffinic hydrocarbon is commingled with about 0.1 to about 10 moles of hydrogen per mole of hydrocarbon.

16. The process of claim 1 wherein said paraffinic hydrocarbon is a $C_4$–$C_9$ alkane.

17. The process of claim 16 wherein said catalytic composite has combined therewith about 1 to about 100 weight percent Friedel-Crafts metal halide, calculated on a metal halide-free composite.

* * * * *